United States Patent [19]
Cook

[11] Patent Number: 5,275,174
[45] Date of Patent: Jan. 4, 1994

[54] REPETITIVE STRAIN INJURY ASSESSMENT

[76] Inventor: Jonathan A. Cook, 65 Strangeways Terrace, North Adelaide, S.A., 5006, Australia

[21] Appl. No.: 913,972

[22] Filed: Jul. 16, 1992

Related U.S. Application Data

[63] Continuation of Ser. No. 731,990, Jul. 18, 1991, abandoned, which is a continuation of Ser. No. 610,308, Nov. 8, 1990, abandoned, which is a continuation of Ser. No. 91,070, Aug. 12, 1987, abandoned.

[30] Foreign Application Priority Data

Oct. 30, 1985 [AU] Australia ............................. PH03180
Feb. 3, 1986 [AU] Australia ............................. PH04419

[51] Int. Cl.$^5$ ................................................. A61B 5/11
[52] U.S. Cl. ...................................... 128/774; 128/782; 128/733; 482/114; 482/115
[58] Field of Search ....................... 128/774, 782, 733; 33/511, 512, 515; 482/114, 115, 121, 122; 73/379

[56] References Cited

U.S. PATENT DOCUMENTS

| | | | |
|---|---|---|---|
| 3,929,335 | 12/1975 | Malick | 340/573 X |
| 4,291,705 | 9/1981 | Severinghaus et al. | 128/733 |
| 4,436,099 | 3/1984 | Raftopoulos | 128/774 X |
| 4,566,461 | 1/1986 | Lubell et al. | 128/707 X |
| 4,595,018 | 6/1986 | Rantala | 128/733 |
| 4,641,832 | 2/1987 | Mattox | 272/131 |
| 4,649,934 | 3/1987 | Fraser et al. | 128/774 X |
| 4,664,130 | 5/1987 | Gracovetsky | 128/733 X |
| 4,667,685 | 5/1987 | Fine | 128/782 |

OTHER PUBLICATIONS

Isotechnologies, Inc. brochure entitled "The dynamic new dimension in sports medicine" (publication date unknown).
Isotechnologies Research Report entitled "What are you really measuring?" (publication date unknown).
Isotechnologies Research Report entitled "Isodynamic Evaluation of Ankle and Foot Function For Taped and Barefoot Conditions" date May 1984.
Isotechnologies Research Report entitled "Dynamic Performance Analysis" dated Jun. 13, 1982.
Isotechnologies, Inc. brochure on Isostation A-100 (publication date unknown).
Isotechnologies brochure entitled "We've changed the way you think about backs" (publication date unknown).

*Primary Examiner*—Ruth S. Smith
*Attorney, Agent, or Firm*—Fish & Richardson

[57] ABSTRACT

A method is described of assessment of a physiological state of a body joint of an animal, wherein a first body portion is connected to a second body portion and is moveable relative to the second body portion through muscular contraction. The method includes the steps of fixing the first body portion with a stationary support, restraining the second body portion with a sleeve capable of motion within a plane, applying a first selected level of resistance to the motion of the sleeve which is constant regardless of the force applied to the sleeve, and contracting the muscle in an effort to produce maximum relative movement within the plane. The rate of change of position of the second body portion is then measured during a plurality of contracting steps. Subsequently, a second selected level of resistance is applied to the motion of the sleeve which is constant regardless of the force applied to the sleeve, the muscle is again contracted in a maximal effort, and a second rate of change of position of the second body portion is measured. A system for assessment of the physiological state of a body joint is also described, including a stationary support to fix the first body portion, a sleeve to receive the second body portion and providing at least first and second levels of constant resistance to relative movement within the plane, and a device for measuring rate of change of position upon maximal exertion.

16 Claims, 9 Drawing Sheets

REPETITIVE STRAIN INJURY ASSESSMENT

This application is a continuation of United States application Ser. No. 07/731,990, filed Jul. 18, 1991, now abandoned which is a continuation of Ser. No. 07/610,308, filed Nov. 8, 1990, now abandoned, which is a continuation of Ser. No. 07/091,070, filed Aug. 12, 1987, now abandoned.

This invention is both a method and means related to providing objective information regarding physiological status surrounding a body joint and muscular and tendon status related to the joint.

Various attempts have hitherto been made to provide an objective assessment of such a physiological status.

It is relatively self-evident that the availability of such information which is less dependent than hitherto on volunteered responses, is of importance especially but not limited to cases where due to caused or perceived trauma, an organic pathology is claimed.

Such a claim can result in very significant compensation costs, and in many cases an inability to properly diagnose the specific pathology and provide an appropriate treatment and, of course monitor such results in an objective way.

According to this invention, it has been discovered that if a joint is caused to be used by the subject, and that there is applied during such movement, a resistance which is at least substantially consistent through a range of movement, and the subject applies a greatest effort to effect such movement, (i.e., the resistance is constant regardless of the force applied to the sleeve) then, information concerning the rate of change of position achieved can provide information that can be of significant value in an assessment of the status surrounding that joint.

Further, however, by measuring electrical activity within muscles controlling the movement of that joint including both an agonist and antagonist, will provide a correlation which when compared to results of other bodies, can further again provide information which is less dependent upon any volunteered response by the subject.

Indeed, in experiments thus far conducted, it has been found that when the results of a subject are compared in respect of others considered normal, and within a similar age bracket and within a similar size and of the same sex, then further valuable assessment of the results can be achieved.

Such valuable results appear at first to indicate the potential for a subject in respect of the joint being tested to be vulnerable to fatigue which may indicate significant vulnerability to developing repetitive strain injury syndrome.

In other cases, however, the organic pathology assessment can indicate lateral epicondylitis of the humerus or other known difficulties.

The invention in one form can be said to reside in method of assessment of a physiological state of a portion of an animal portion wherein the body portion is moveable relative to an adjoining portion with muscular interaction, the method being characterised in that a first body portion is retained with respect to a first member, and a second body portion is retained in respect to a second member, relative movement between the said two members being constrained with selected levels of resistance, the relative movement being caused by action of the muscles between the body portions, and means recording a rate of change of position of such movement against a selected level of resistance for a perceived effort to effect such movement through a plurality of repeat movements.

In order to provide an effective assessment, the extent of perceived effort must be assessed and this can be a reliance upon a request that the subject apply a best effort in respect of the movement.

Where, however, this may not be forthcoming or may be suspected as not being offered, there is then provided according to this invention means to measure the extent of electrical activity triggering at least one of the muscles effecting the motion during such effort.

It has been found, however, that the status of both an agonist and antagonist muscle controlling the joint can have a significant influence over the result and hence in preference, there are means to both measure the extent of electrical activity triggering in respect of both selected agonist and antagonist muscles in response to the resultant rate of change of position of movement achieved from this.

There can be some difficulties in respect of some joints where either the same muscles or other muscles in close collaboration effect additional pressures and where such additional pressures may be offering a different degree of electrical effect, there is provided according to this invention means to separately assess such additional effect so as to provide a better assessment of the objective level of the muscles directly effecting the movement of the joint.

In this respect, when the movement of a wrist is examined, the extent of grip effected at the same time can significantly alter the results and hence there shall be provided means to assess such additional effects and provide an assessment for extraction of such results from directly controlling muscle effects in preference there being means to assess muscles acting as agonist and those acting as antagonist.

In preference, an assessment of rate of change of position can be achieved by a measurement of a relative position of one part of the body portion as compared to the other when recorded against a selected time base so that the gradient of such a change of position at a given time can indicate the rate of change of position achieved of the particular body portion.

As such rate of change of position is achieved by rotation by one part of a body as compared to another, it will be well understood that the resistance is effected at a distance by providing the resistance as rotational torque resistance.

The invention in a further form can be said to reside in apparatus for assessment of the physiological state of a body portion where the body portion is movable relative to an adjoining portion with muscular interaction, said apparatus being characterised in that there are provided means to hold one of the body portions relative to another, and there are means to engage with said second body portion and provide a consistent resistance to motion of the said second body portion relative to the first said body portion, and there are means to record the rate of change of position achieved by any such motion.

In preference, there are means to select different levels of resistance.

In preference, there are means to record the electrical activity triggering respective muscles effecting joint movement and recording such effects against a common time base with respect to the rate of change of position achieved of the movement of the body portion in response to such muscular action relative to the other body portion.

Experiments thus far conducted have indicated significant value in respect to such tests associated with the wrist of a human wherein there is provided clamp means to hold a forearm of the person, a crank having a pivot axis which can be aligned with respect to the wrist axis of the subject arm, a handle on the crank adapted to be gripped by the subject hand, means with the handle to assess a level of grip effected, means rotatable by the crank which can be caused to effect a consistent resistance through any rotational position of the crank about its supporting axis, and means to record a relative position of the crank against a selected time base whereby to provide rate of change of position of motion achieved through any such required action.

The invention will generally be better understood when described with respect to a preferred embodiment, at which time some information as to the value of the assessment technique will also be offered with respect to specific subject instances.

Accordingly the invention will now be described with reference to the preferred embodiment which shall be described with the assistance of drawings in which.

Figure 4:
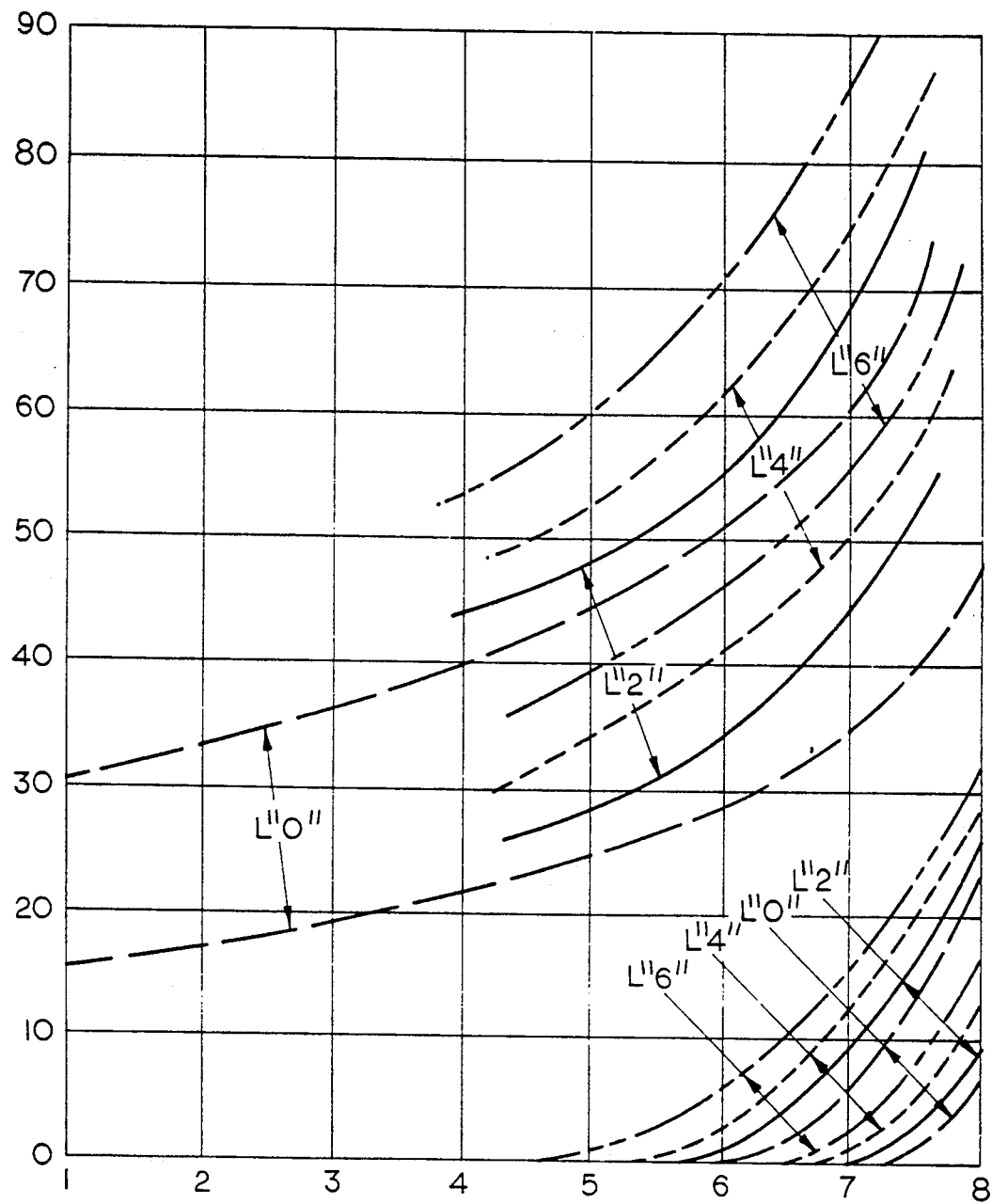
Figure 5:
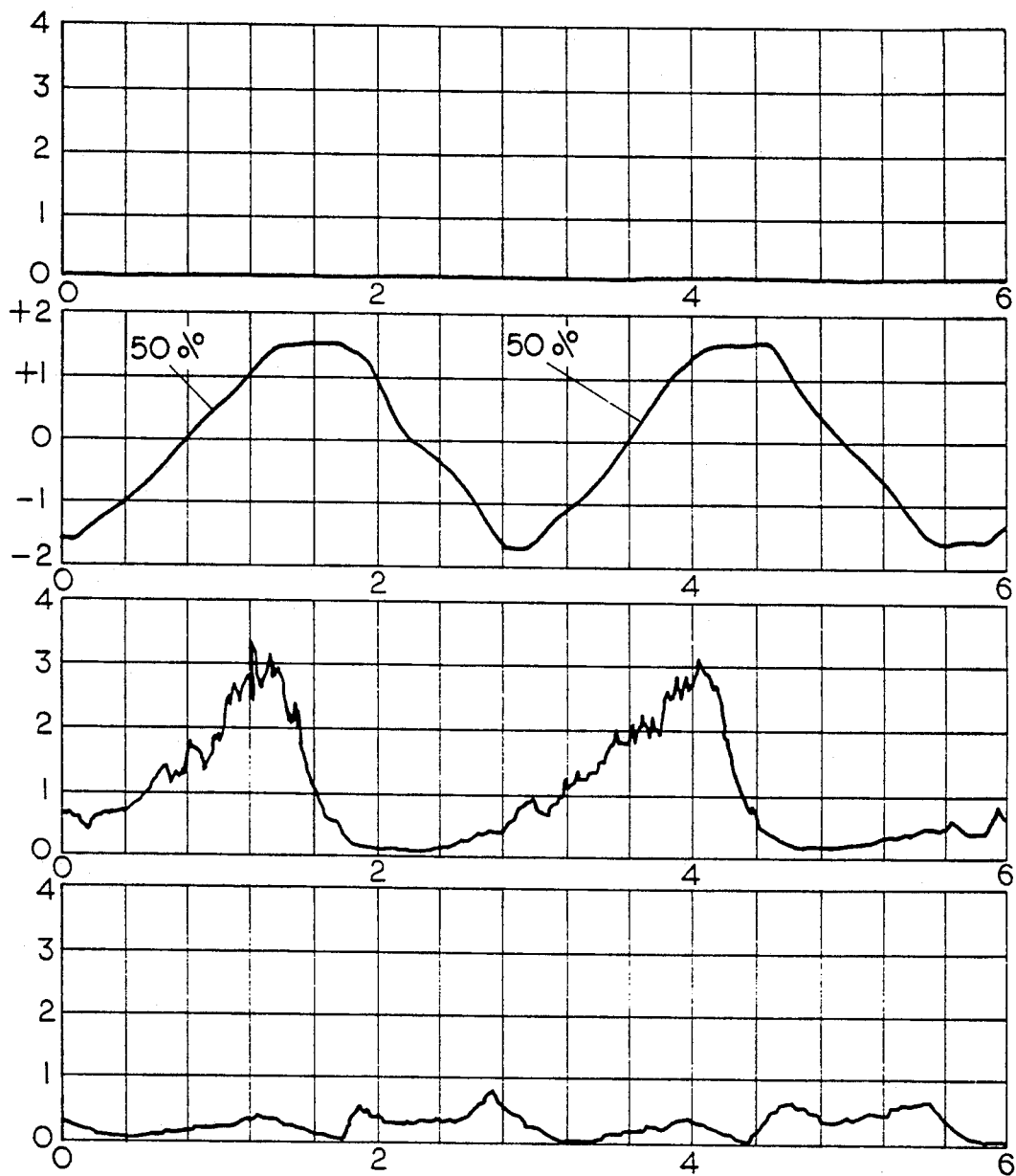
Figure 6:
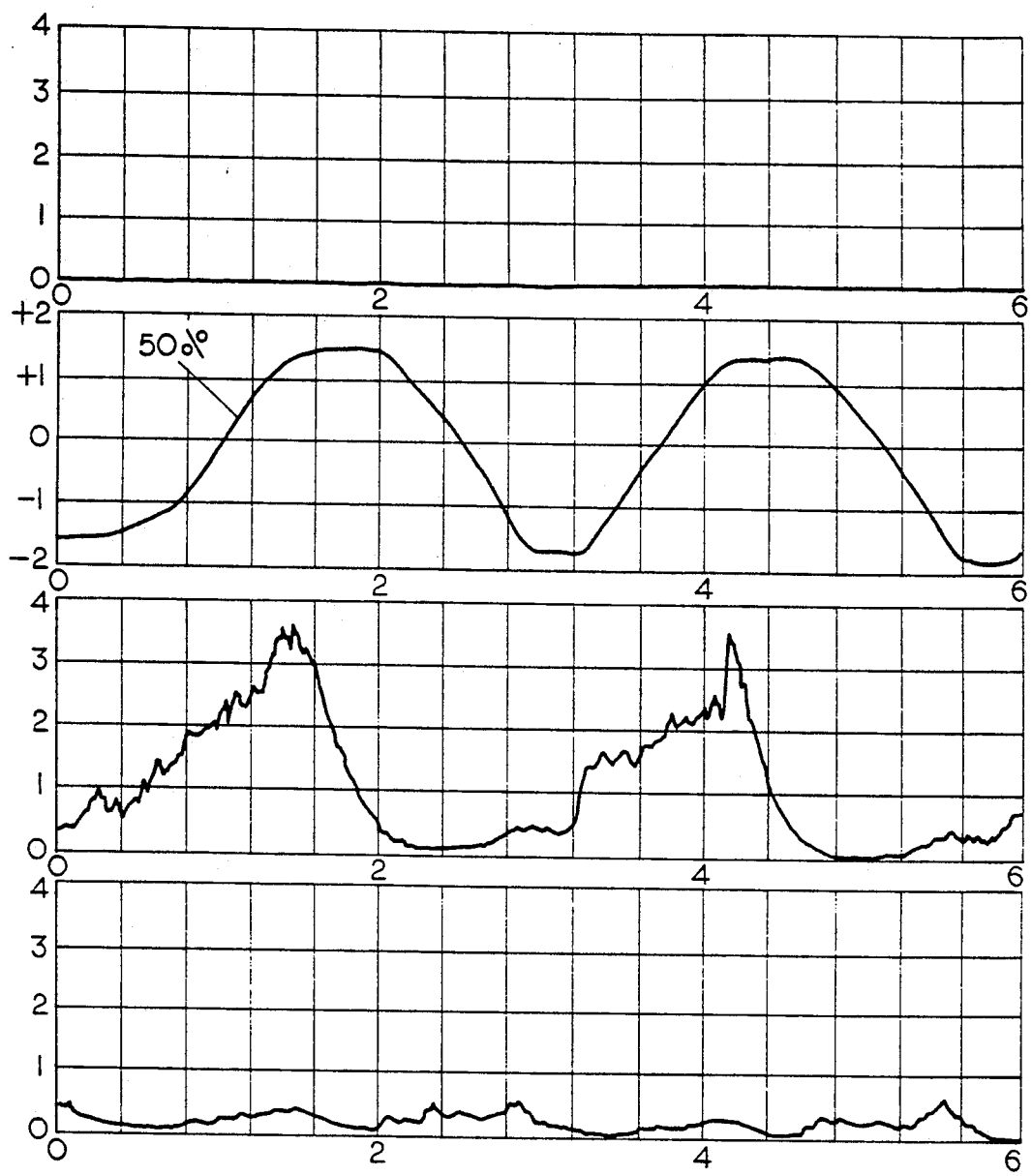
Figure 7:
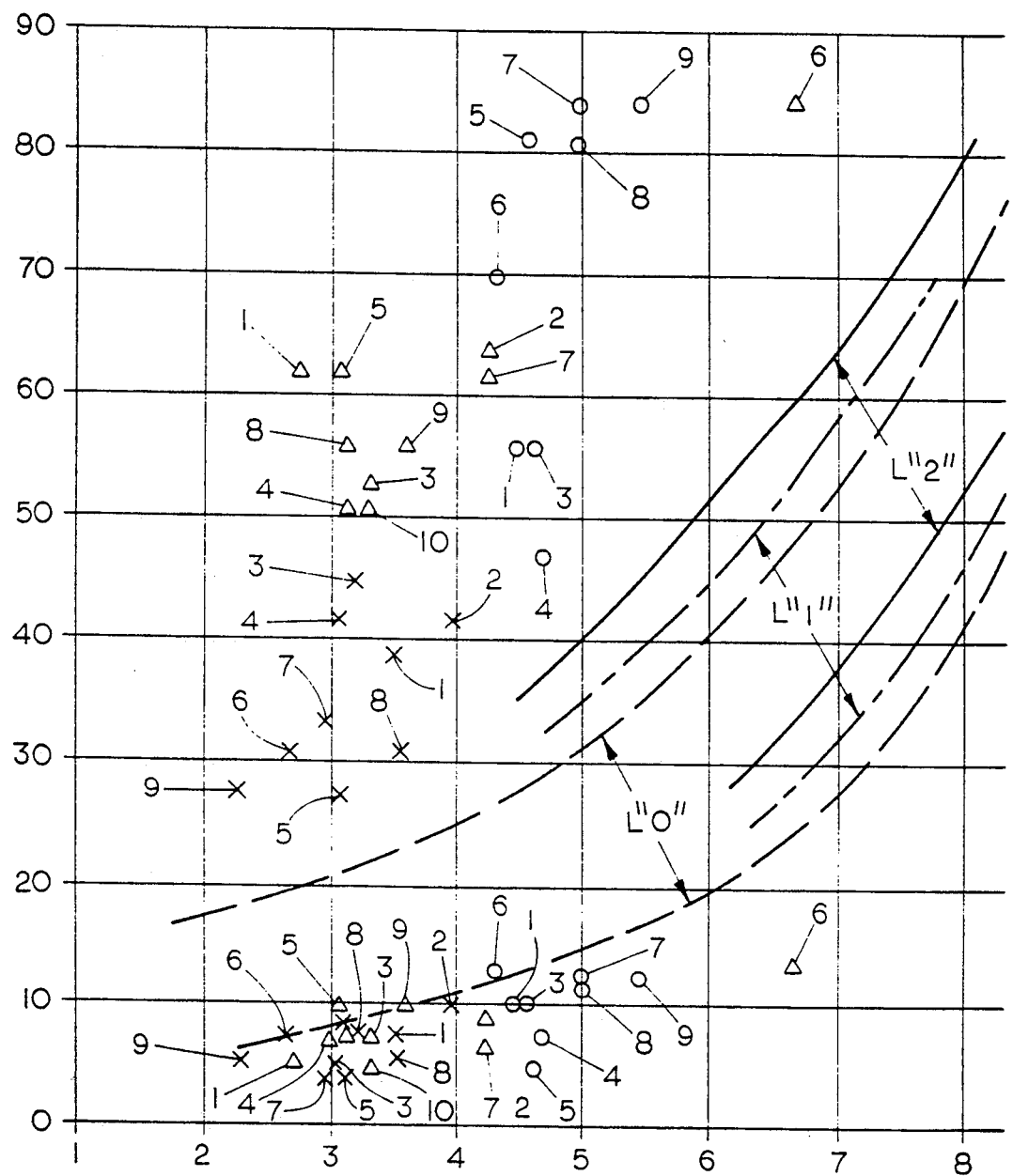
Figure 8:
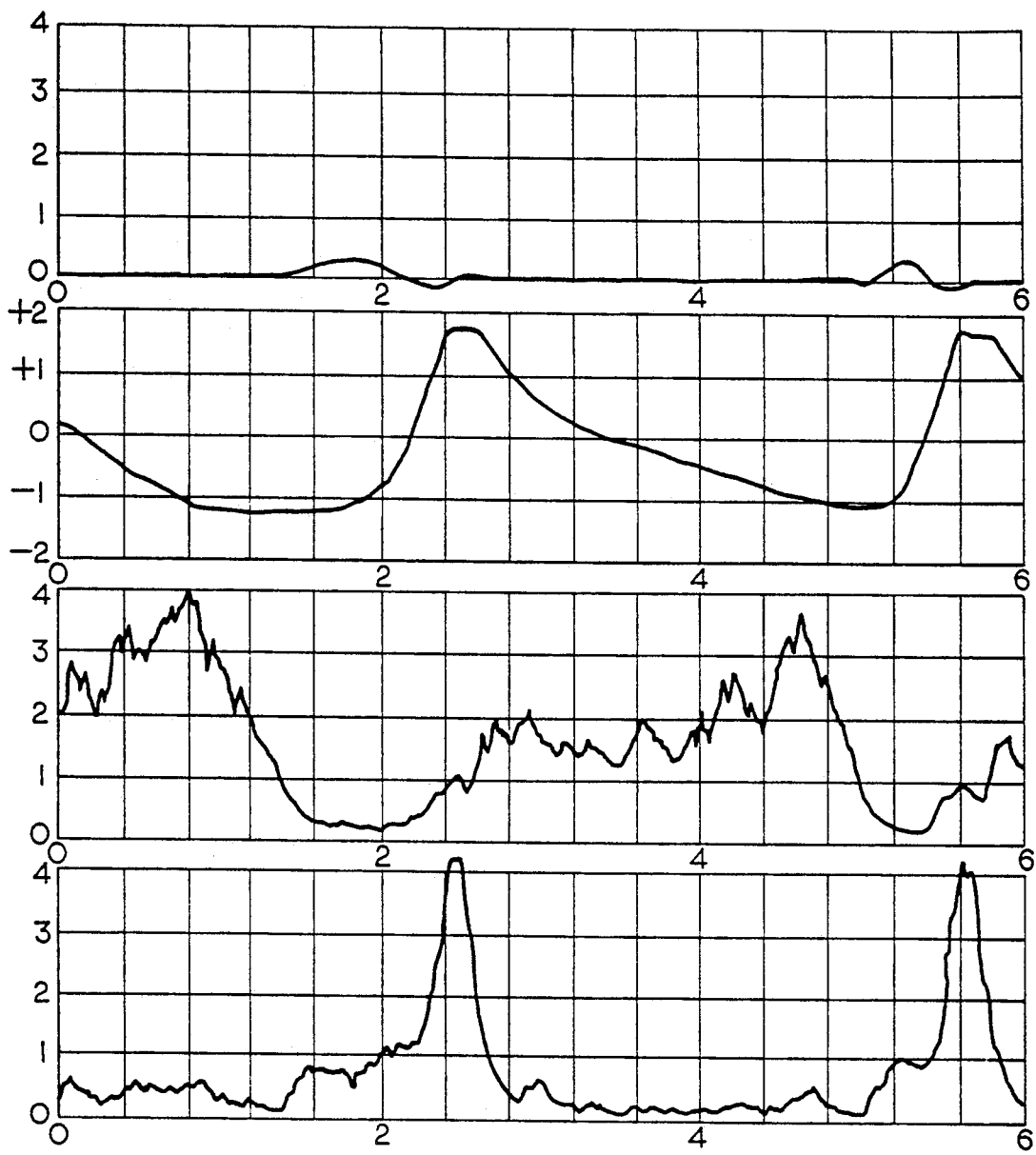
Figure 9:
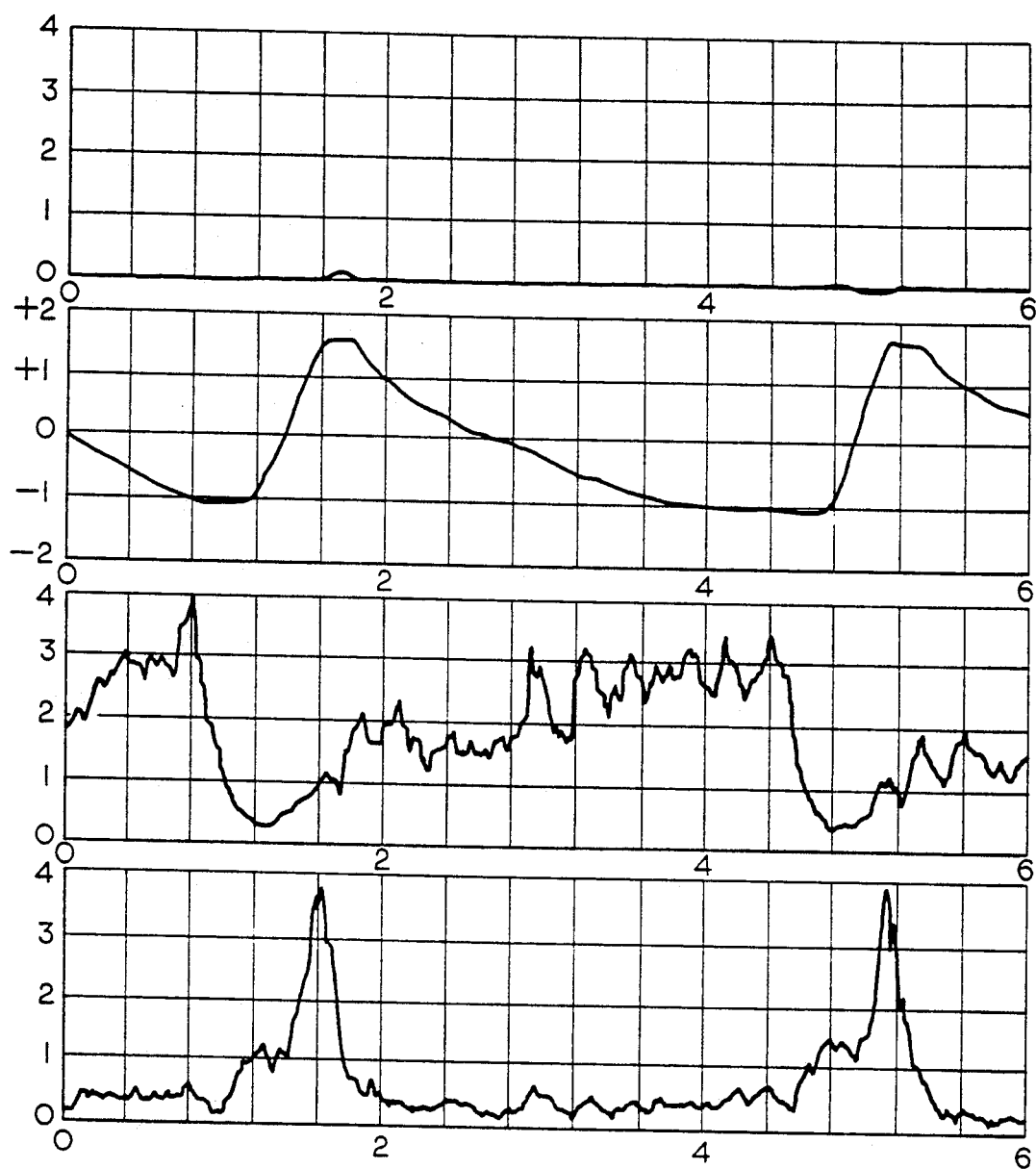

FIG. 4 illustrates in a graphical arrangement, an illustration of the ranges within which a normal physiological status can be observed against as a vertical axis the extent of electrical activity as a percentage of selected maximum, and across the base, degrees gradient which is a measure of the tangential angle of the graphical position of the moved body portion against a given time base, this thereby indicating a speed of motion, and the respective levels in ranges, indicating results in respect to a selected relative resistance, level O being a lowest resistance and level 6 (18 inch-pounds rotational torque) being a highest selected resistance the upper ranges being for the agonist and the lower ranges being for antagonist;

FIG. 5 is a reproduction of actual results in respect of subject A showing from top to bottom, an assessment of electrical activity provided by grip, the relative position of the hand relative to the forearm, the extent of electrical activity in the agonist muscle extensor difitorum, and finally the extent of electrical activity in the antagonist muscle flexor carpi radians, all of these against a common time base which is in fact 25 MMS per second, these results being recorded against a level 4 resistance (that is 12 inch-pounds rotational torque);

FIG. 6 illustrates in same arrangement as for FIG. 5, the same subject A in respect to the same motion, in this case in respect of an increased level resistance 6;

FIG. 7 illustrates graphical results illustrating a person having clinically established organic pathology for a non-dominant wrist extension the subject being a female aged 57 years and having a height of 5'3", there being shown on the graph expected predicted level ranges, in the one case for level 2, and in another case at level 0 the actual results being shown for readings of level O the cross, level 1 (3 inch-pounds) the triangle and for level 2 (6 inch-pounds) the circle, the agonist readings being those all above 20% electrical activity line and the antagonist all those below this, and FIGS. 8 and 9 are the same readings as in FIGS. 5 and 6 against the same time base, in respect of FIG. 8 this being an action against level 1 resistance, and in the case of FIG. 9 this being an action again by subject B against a level 2 resistance.

Figure 1:
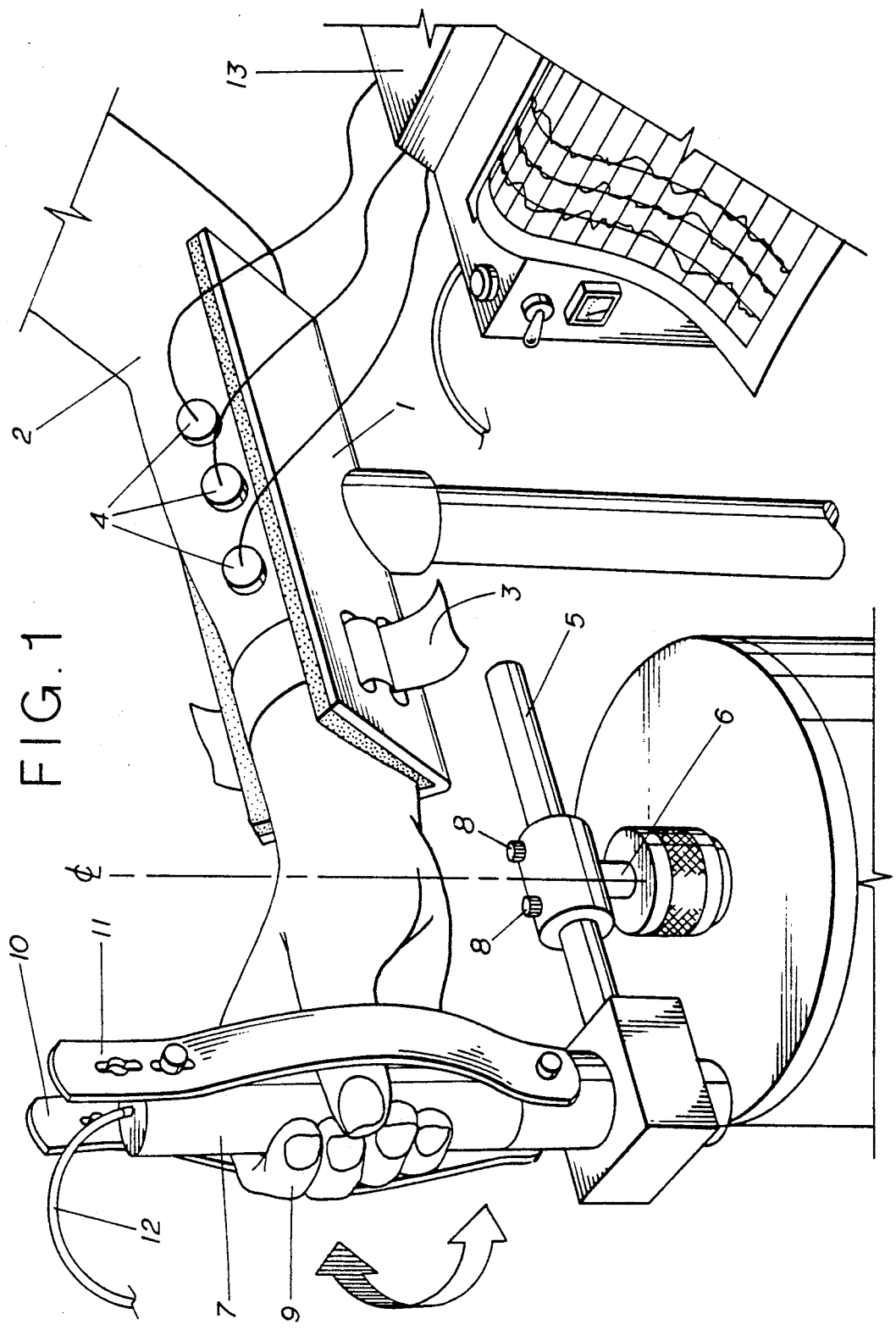
FIG. 1 is a perspective view of an assembly incorporating a subject arm in a chest position.
Figure 2:
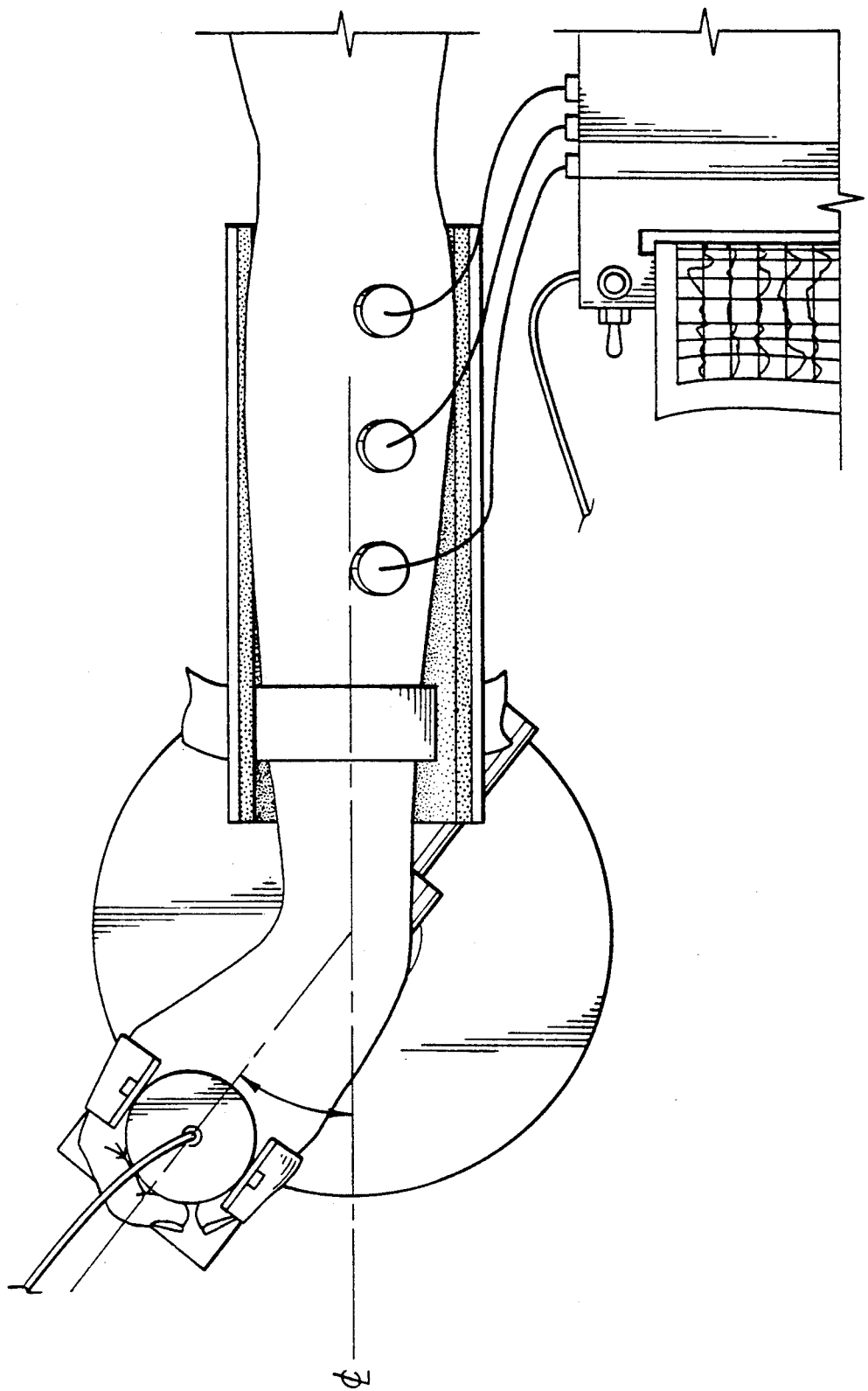
FIG. 2 is a plan view of the same arrangement as in FIG. 1.
Figure 3:
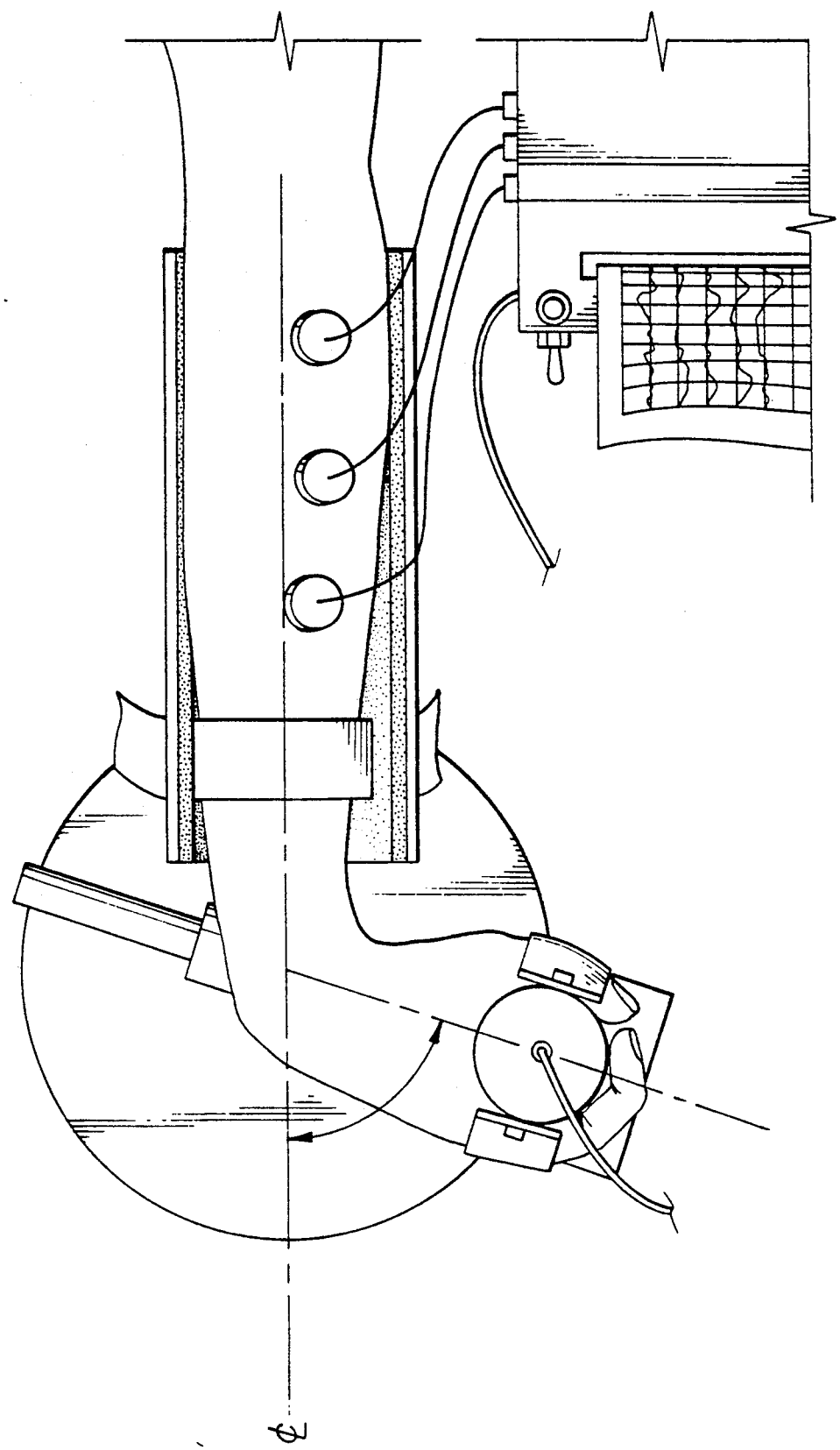
FIG. 3 is the same plan view as in FIG. 2 with the position of the hand relative to the forearm being moved through a full extent of turn.

Referring in detail to the drawings, and in particular to FIGS. 1, 2 and 3, there is shown a cradle 1 into which the forearm 2 of a subject is located positively by reason of its laterally extended v-shape, and a strap 3 is available to be tightened across the forearm whereby to relatively rigidly affix the location of the forearm 2.

By way of example, there is shown attached at relative positions along an agonist muscle of the forearm, three electrical detectors 4, the position of each of these detectors being established by clinical observation so that they are positively located over the centre of the belly of the selected muscle, that the surface of the forearm is appropriately treated, included if necessary the removal of insulating hair, and the addition of a conducting cream, which, however, should not extend between the respective electrodes so that there is no cross interference.

While there are shown three electrodes on a muscle which is indicated as being an agonist, an appropriate antagonist is also selected so that the results from both the agonist and antagonist muscles, as later illustrated, can be assessed against the same time base.

The location of each electrode must be located by a person able to clinically establish the location of the respective muscle and the position of each electrode should then be established so that the electrode is over the middle or belly part of the muscle and in each case a selected distance from the point of origin of the respective muscle. The illustration is showing only in the most schematic way the existence of electrodes rather than the exact alignment.

The selection of position of the electrodes for a wrist has been found to be best located in the case of the extensors of the wrist, at each of a 10%, 20% and 30% position of the full length of the muscle from the point of origin of the muscle and in respect of the flexor of the muscle, at a 15%, 25% and 35% from the point of origin of the muscle. In each case, the readings have been taken from each of the electrodes and the average on a route mean square basis has been taken for subsequent reference purposes.

It is to be emphasised that the magnitude of electrical activity is assessed for any one person with a common setting so that the readings are consistent in relative terms.

However, considerable value has been found in providing a reference level which can be assessed independent of any voluntary control by the subject.

Accordingly, a 100% electrical activity magnitude reference can be obtained when a full exertion from full flexion to full extension of the wrist (in the case of the wrist) occurs the exertion being at a medium rate of change and the level of resistance being negligible or in other terms "level O". The electrical activity established at the point of full extension can then be used as the so called 100% reference figure in that it has been found as previously stated that there appears to be a consistent magnitude which does not depend upon volunteered responses and in relation to which subsequent electrical activity can be assessed.

Both the agonist and antagonist muscles can be used to establish in each case the so called 100% electrical activity reference figure for each muscle and in each case against a level 0 for full wrist flexion and this provides good assessment for comparing further electrical activities.

Further to the forearm being located in a fixed position, the orientation about a lateral axis is also of relevance so that the axis of the wrist will be generally coincident with the axis of a crank, a rotor axis 6 being connected to an electrical stator and rotor combination configured and driven such that by a selected current input into respective coils within the device, there will be caused a consistent selected level of resistance against any motion of rotation of the axis 6. Such technology is readily available.

In respect of such selected resistance, however, the extent of relative position of the grip 7 is adjusted by release of several adjustment nuts 8 so that a best and most comfortable gripping position for the hand 9 can be achieved while maintaining the coincidence of the axis of alignment of the wrist joint with the rotor 6.

Furthermore, however, there are means confining the position of the hands, namely straps 10 and 11.

The grip 7 is internally arranged so that by means of an assessment of the internal pressure caused around the grip, this will cause a change in resistance in sensitive material which thereby provides an assessment of the extent of grip providing an electrical voltage available through connection 12 which is used to provide one of the reference measurements proportional to grip used on the chart recorder 13.

There are, of course, separate electrical controls providing for affixing of resistance against rotation of the rotor 6 and with this arrangement in place, a first resistance level arbitrarily selected as level 0, is selected and the subject is told to move with maximum possible effort the hand through a maximum movement range and to repeat such movements reciprocally through eight repeats for such movement.

It has been found that with a given rate of change of position at a medial point through such an extension range when correlated against the extent of electrical activity provided within the agonist muscle controlling such movement, then there appears in relation to expected and observable criteria of a person, a range of positions which can be realistically assessed as within a normal expected range for the joint of a non pathologically affected person of the selected height, and of the same sex and similar age.

The degree of accuracy of such an assessment will depend on a number of factors.

It has been observed, however, that for a person wishing to maintain a deliberately slow speed, there appears to be no antagonist electrical activity at a lowest level of resistance with only slight increase of this activity at higher levels of resistance as regards the median position of the wrist.

Further, however, for those exhibiting significant organic pathology, the marked shift by requiring significantly more activity with the same or a lesser rate of change of position resulting, and/or more observable antagonist activity, can indicate, in the experiments thus far conducted that there is some organic pathology and such indication can be independent of any volunteered information from the subject.

In a further situation, where the results indicate for the same electrical activity magnitude, a lesser rate of change of position can also indicate organic pathology.

While the word "pathology" is used, it is intended that this be illustrative and not limiting in defining the value to which the method and apparatus can be put. For instance, the method has significant value on the results thus far assessed in indicating an organic physiological status which can be indicative of the fitness of the muscles controlling the joint concerned. Accordingly, some indication of fitness in the athletic sense can be gained in a quantitive manner.

It must be emphasised that the extent of testing thus far has only illustrated that a significant proportion of those with organic pathology may indicate different results by which means there can be a relative assessment and appropriate reasonable diagnosis made.

Both the rate of change of position achieved, and the electrical activity, however, are referred to by relative levels so that recognition of an organic pathology depends upon a significant base of normal references and therefore an accurate assessment of a normal spread of such results taken for similar resistance levels and in respect of those people who have similar age, height and sex. Such factors as the dominance of a left arm as compared to a right arm must also be taken into account.

This will very directly depend therefore upon the numbers of samples against which references can be made and in due course this will be significantly improved even though the assessment technique can remain substantially the same.

The results thus far have been able to indicate the existence of organic pathology which has been separately observable by clinical methods, and as such the relative figures have been vindicated.

Accordingly, FIGS. 5 and 6 indicating typical readings taken from a normal subject, illustrate minimal grip interference, and at level 4 (12 inch-pounds rotational torque) a gradient which is an assessment of speed of 50° at a 50% median location between a maximum of extension and a maximum of flexion in each case of the wrist, and for these levels of resistance, the relative magnitude of electrical activity being assessed as a percentage of the reference assessment as previously obtained in respect of the so called 100% electrical activity against a level 0 resistance as above identified.

The bottom line of FIG. 5 and of FIG. 6 illustrating the extent of the antagonist electrical activity can indicate any effect of anomalous caustive action caused by voluntary attempts at alteration with any result. Antagonist electrical activity can indicate of itself especially at lower resistance levels and slow rate of change of position muscle spasm and to this extent organic pathology. For instance, the magnitude of electrical activity for the antagonist may be higher than normal while the agonist may remain high through the exertion.

Conversely, with voluntary slowing there may appear an increase in antagonist electrical activity and a decrease in antagonist activity at the point of slowing.

While reference has been made to an assessment at a mid point between the extension and flexion further information can be gained in assessment at other location points.

The remaining references, that is in FIG. 6 and in the graph 7 and the typical results at FIGS. 8 and 9, are given to indicate the approach presently taken to make best use of the results achieved thus far.

The results of themselves have to be interpreted and as against a basis of controls, used to assist in a final assessment in an objective way of such results as are obtained.

While reference has now been made to the specific case of a wrist as being the arm of a person, such specific technique will illustrate the method which can be applied to other parts of a body.

For use of the method and similar apparatus in respect of other body portions, reference will now be made to typical other parts of the body.

Reference the elbow joint.

In the elbow joint, the biceps brachii cause flexion of the elbow and the triceps brachii on contraction cause extension of the elbow. In the same way as with the forearm and wrist, the subject is required to locate the upper arm in a resting cradle secured by a restraining strap, the elbow being placed on an elbow rest at the pivot point where a tool is inserted and this tool would have the capacity to change in length and have an upright bar for the patient to grasp providing a crank effect so that there will be again a rotor having a common axis with the axis of the elbow.

For the neck of a person, the patient shall sit, a head restraining device being connected to a rod which would have complete freedom of rotation of the rod providing thereby no resistance to movement of the head restraining device in a rotational manner about an essentially vertical axis, but, there is provided a crank connecting through to a rotational rotor having a parallel axis with the joint to be tested.

The same principles can apply to the lumbo-sacral spine where a restraining device can be positioned firmly against the anterior antero-lateral and posters-lateral chest wall with the attachment from this restraining device going to the crank which would effect rotation within the rotor providing the consistent level of resistance selected. The axis of the lumbo-sacral spine should be coincident with the axis of a rotor providing resistance.

As in each of these cases, testing of the respective muscles will require that alternate muscle effects must be allowed for, and accordingly in this case, testing of lumbar flexion extension in the median, or sagittal plane, requires measuring the electromyogram of the erector spinae muscles pilaterally (representing the extensors of the lumbo-sacral spine) and the psoas major/iliacus and the abdominal external oblique muscles causing flexion of the lumbo-sacral spine.

These illustrations are given simply to indicate that the same principles can be applied to any individual part of the body and it is not intended that the invention should be necessarily limited to the specific performance related to the wrist of a human.

This will now illustrate how by using information available in the manner described, an assessment and objective information can be obtained which can be of significant value in respect to aspects related to the animal body.

Such results can be particularly useful in respect to an assessment that where fatigue is seen to occur at a lower than expected level of resistance, correction by way of exercise can be a means for assisting and removing the existing weakness.

The method can also be applicable to objective testing of the physiological status of an animal other than human.

The method and apparatus therefore can be said to provide for an assessment of a fitness status in respect of muscles as applied to body joints.

I claim:

1. A method of assessment of a physiological state of a body joint of an animal wherein a first body portion is connected to a second body portion and is movable relative to the second body portion through muscular contraction, which comprises:

fixing the first body portion by a stationary support;

restraining the second body portion by a sleeve capable of motion within a plane, said plane being defined by a motion of the second body portion about a pivot point of the joint and the second body portion being connected to the first body portion by at least one muscle;

applying a first selected level of resistance to the motion of the sleeve which is constant regardless of the force applied to the sleeve so as to constrain relative movement within the plane, the relative movement being effected by the muscle;

contracting the muscle in an effort to produce maximum relative movement within the plane;

measuring a rate of change of position of the second body portion within the plane during a plurality of contracting steps;

applying a second selected level of resistance to the motion of the sleeve which is constant regardless of the force applied to the sleeve so as to constrain relative movement within the plane, the relative movement being effected by the muscle;

contracting the muscle in a maximal effort to produce maximum relative movement within the plane; and measuring a second rate of change of position of the second body portion within the plane during a plurality of contracting steps.

2. The method of claim 1 wherein the first body portion is a human forearm and the second body portion is a human hand.

3. The method of claim 1 wherein the muscle comprises at least one agonist muscle and at least one antagonist muscle capable of producing the maximum relative movement.

4. The method of claim 1 further comprising the step of determining over a preselected time period the level of electrical activity generated by the muscle during the step of connecting.

5. The method of claim 4 further comprising the step of comparing the level of electrical activity generated by the muscle to the rate of change of position of the second body portion within the plane during a plurality of contracting steps.

6. The method of claim 5 wherein the step of comparing the level of electrical activity to the rate of change of position is performed at a selected medial body portion position.

7. The method of claim 5 further comprising comparing the level of electrical activity and the rate of change of position obtained from a test subject with a normal reference level and rate obtained from matched reference subjects.

8. The method of claim 7 wherein the matched reference subjects are of similar age, sex and height.

9. A method of assessment of a physiological state of a body joint of an animal wherein a first body portion is connected to a second body portion and is movable relative to the second body portion through muscular contraction, which comprises:

fixing the first body portion by a stationary support;

restraining the second body portion by a sleeve capable of motion within a plane, said plane being defined by a motion of the second body portion about a pivot point of the joint and the second body portion being connected to the first body portion by at least one muscle;

applying a selected level of resistance to the motion of the sleeve so as to constrain relative movement within the plane, the relative movement being effected by the muscle;

contracting the muscle in an effort to produce maximum relative movement within the plane;

determining over a preselected time period the level of electrical activity generated by the muscle during the step of contracting;

recording a background level of electrical activity produced by a muscular action that is unrelated to movement of the second body portion about the pivot point of the joint;

subtracting the background level of electrical activity from the level of electrical activity generated by the muscle during the step of contracting; and measuring a rate of change of position of the second body portion within the plane during a plurality of contracting steps.

10. A system for assessment of a physiological state of a body joint of an animal, wherein a first body portion is connected to a second body portion and is movable relative to the second body portion through muscular contraction, which comprises:

a stationary support to fix the first body portion;

a sleeve to receive the second body portion, said sleeve being capable of motion within a plane defined by motion of the second body portion about a pivot point of the joint and providing at least first and second levels of resistance to relative movement within the plane which are constant regardless of the force applied to the sleeve; and means for measuring a rate of change of position of the sleeve within the plane upon maximal exertion at the first and second levels of resistance, whereby the physiological status of the body joint may be assessed.

11. The system of claim 10 wherein the measuring means comprises means for recording a rate of change of position of the sleeve within the plane, said change of position achieved by motion of the second body portion about a pivot point of the joint.

12. The system of claim 10 further comprising means for measuring a level of electrical activity generated by the muscular contraction producing motion of the second body portion about a pivot point of the joint.

13. The system of claim 12 wherein the measuring means comprises means for recording a rate of change of position of the sleeve within the plane, said change of position being achieved by motion of the second body portion about a pivot point of the joint.

14. The system of claim 10 further comprising means for selection of different levels of constant resistance to relative movement within the plane.

15. The system of claim 10 wherein the sleeve is rotatably connected to a rotor shaft having an axis of rotation substantially coincident to a pivot point of the body joint.

16. A system for assessment of a physiological state of a body joint of an animal, wherein a first body portion is connected to a second body portion and is movable relative to the second body portion through muscular contraction, which comprises:

a stationary support to fix the first body portion;

a sleeve to receive the second body portion, said sleeve capable of motion within a plane defined by motion of the second body portion about a pivot point of the joint and capable of providing a constant resistance to relative movement within the plane;

means for measuring a level of electrical activity generated by the muscular contraction producing motion of the second body portion about a pivot of the joint;

means for recording a background level of electrical activity produced by a muscle contraction that is unrelated to movement of the second body portion about a pivot point of the joint; and means for measuring a rate of change of position of the sleeve within the plane, whereby the physiological status of the body joint may be assessed.

* * * * *

REEXAMINATION CERTIFICATE (3589th)

United States Patent [19]

Cook

[11] B1 5,275,174

[45] Certificate Issued Aug. 4, 1998

[54] REPETITIVE STRAIN INJURY ASSESSMENT

[76] Inventor: Jonathan A. Cook, 65 Strangeways Terrace, North Adelaide, S.A., 5006, Australia

Reexamination Request:
No. 90/003,683, Dec. 29, 1994

Reexamination Certificate for:
Patent No.: 5,275,174
Issued: Jan. 4, 1994
Appl. No.: 913,972
Filed: Jul. 16, 1992

Related U.S. Application Data

[63] Continuation of Ser. No. 731,990, Jul. 18, 1991, abandoned, which is a continuation of Ser. No. 610,308, Nov. 8, 1990, abandoned, which is a continuation of Ser. No. 91,070, Aug. 12, 1987, abandoned.

[30] Foreign Application Priority Data

Oct. 30, 1985 [AU] Australia ............................ PH03180
Feb. 3, 1986 [AU] Australia ............................ PH04419

[51] Int. Cl.$^6$ .................................................. A61B 5/11
[52] U.S. Cl. ........................... 600/587; 600/546; 600/595; 482/114; 482/115
[58] Field of Search .................................. 128/733, 774, 128/782; 73/379; 482/114, 115, 121, 122; 600/546, 587, 595

[56] References Cited

PUBLICATIONS

Tihanyi et al., "Force–Velocity–Power Characteristics and Fiber Composition Characteristics in Human Knee Extensor Muscles", vol. 48, *European Journal of Applied Physiology*, pp. 331–343 (1982).

Pertuzon et al., "Instantaneous Force–Velocity Relationship in Human Muscle", vol. 8, *Medicine and Sport, Biomechanics III*, pp. 230–234 (Karger, Basel 1973).

DeKoning et al., "Influence of Static Strength Training on the Force–Velocity Relationship of the Arm Flexors", *International Journal of Sports Medicine*, vol. 3, pp. 25–28 (1982).

Wilkie, "The Relation Between Force and Velocity in Human Muscle", *Journal of Physiology*, vol. 110, pp. 249–280 (1950).

Chapman et al., "The Use of Muscle Stretch in Inertial Loading", *Muscle Stretch in Inertial Loading, Biomechanics IX-A*, Proceedings of the Ninth International Congress of Biomechanics held in 1983 at Waterloo, Ontario, Canada, pp. 45–49 (1985).

(List continued on next page.)

*Primary Examiner*—Ruth S. Smith

[57] ABSTRACT

A method is described of assessment of a physiological state of a body joint of an animal, wherein a first body portion is connected to a second body portion and is moveable relative to the second body portion through muscular contraction. The method includes the steps of fixing the first body portion with a stationary support, restraining the second body portion with a sleeve capable of motion within a plane, applying a first selected level of resistance to the motion of the sleeve which is constant regardless of the force applied to the sleeve, and contracting the muscle in an effort to produce maximum relative movement within the plane. The rate of change of position of the second body portion is then measured during a plurality of contracting steps. Subsequently, a second selected level of resistance is applied to the motion of the sleeve which is constant regardless of the force applied to the sleeve, the muscle is again contracted in a maximal effort, and a second rate of change of position of the second body portion is measured. A system for assessment of the physiological state of a body joint is also described, including a stationary support to fix the first body portion, a sleeve to receive the second body portion and providing at least first and second levels of constant resistance to relative movement within the plane, and a device for measuring rate of change of position upon maximal exertion.

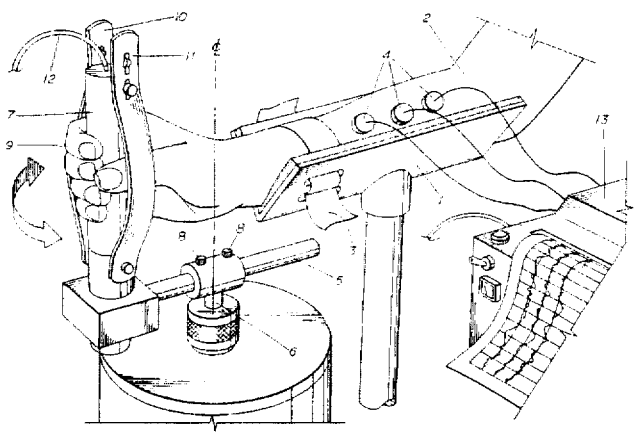

OTHER PUBLICATIONS

Stothart, "Relationships Between Selected Biomechanical Parameters of Static and Dynamic Muscle Performance", *Medicine and Sport, Biomechanics III*, vol. 8, pp. 210–217 (Karger, Basel 1973).

Hof et al., "EMG to Force Processing II: Estimation of Parameters of the Hill Muscle Model for the Human Triceps Surae by Means of a Calfergometer", *Journal of Biomechanics*, vol. 14, No. 11, pp. 759–770 (1981).

Biodex Sales Brochure including price list, describing machines sold by Biodex Corporation for exercise and tests according to demands of orthopaedic and sports medicine, seven pages (May 1, 1985).

Sales Brochure from Isotechnologies, Inc. entitled "File: Human Performance Testing/Low Back" describing the Isostation B–100 Machine sold by Isotechnologies, Inc. for evaluation of motion of the low back (undated).

Sales brochure from Isotechnologies, Inc. entitled "File: Human Performance Testing—Ankle/Subtalar", describing the Isostation A–100 Machine sold by Isotechnologies, Inc. for measuring plantar flexion/dorsiflexion, inversion/eversion, or the two in combination simultaneously.

Seeds et al., "Normative Data for Isostation B–100", Journal of Orthopaedic and Sports Physical Therapy, vol. 9, No. 4, pp. 141–155 (1987) *Note: Seeds et al. is not prior art, but contains a discussion of the prior art Isostation B–100 Machine.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, lines 24–25:

Furthermore, however, there are means confining the position of the hands, namely straps 10 and 11, *that together with the grip 7 form a movable restraining member.*

Column 7, lines 13–40:

In the elbow joint, the biceps brachii cause flexion of the elbow and the triceps brachii on contraction cause extension of the elbow. In the same way as with the forearm and wrist, the subject is required to locate the upper arm in a resting cradle secured by a restraining strap, the elbow being placed on an elbow rest at the pivot point where a tool is inserted and this tool would have the capacity to change in length and have an upright bar for the patient to grasp (*i.e., a movable restraining member*) providing a crank effect so that there will be again a rotor having a common axis with the axis of the elbow.

For the neck of a person, the patient shall sit, a head restraining device (*i.e., a movable restraining member*) being connected to a rod which would have complete freedom of rotation of the rod providing thereby no resistance to movement of the head restraining device in a rotational manner about an essentially vertical axis, but, there is provided a crank connecting through to a rotational rotor having a parallel axis with the joint to be tested.

The same principles can apply to the lumbo-sacral spine where a restraining device (*i.e., a movable restraining member*) can be positioned firmly against the anterior antero-lateral and posters-lateral chest wall with the attachment from this restraining device going to the crank which would effect rotation within the rotor providing the consistent level of resistance selected. The axis of the lumbo-sacral spine should be coincident with the axis of a rotor providing resistance.

AS A RESULT OF REEXAMINATION, IT HAS BEEN DETERMINED THAT:

Claims 1–16 are cancelled.

\* \* \* \* \*